(12) United States Patent
Ito et al.

(10) Patent No.: US 10,898,470 B1
(45) Date of Patent: Jan. 26, 2021

(54) PHARMACEUTICAL COMPOSITION CONTAINING ANTIFUNGAL AGENT AS ACTIVE INGREDIENT

(71) Applicant: SATO PHARMACEUTICAL CO., LTD., Tokyo (JP)

(72) Inventors: Masahiro Ito, Yokohama (JP); Kiyotaka Matsui, Kawasaki (JP); Masami Inuma, Atsugi (JP)

(73) Assignee: SATO PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/730,731

(22) Filed: Dec. 30, 2019

(30) Foreign Application Priority Data

Aug. 13, 2019 (JP) ................. 2019-148620

(51) Int. Cl.
| | | |
|---|---|---|
| *A61K 31/4178* | (2006.01) | |
| *A61K 47/12* | (2006.01) | |
| *A61K 47/08* | (2006.01) | |
| *A61K 47/10* | (2017.01) | |
| *A61P 31/10* | (2006.01) | |
| *A61K 47/32* | (2006.01) | |
| *A61K 9/00* | (2006.01) | |
| *A61K 47/22* | (2006.01) | |

(52) U.S. Cl.
CPC ........ *A61K 31/4178* (2013.01); *A61K 9/0014* (2013.01); *A61K 47/08* (2013.01); *A61K 47/10* (2013.01); *A61K 47/12* (2013.01); *A61K 47/22* (2013.01); *A61K 47/32* (2013.01); *A61P 31/10* (2018.01)

(58) Field of Classification Search
None
See application file for complete search history.

(56) References Cited

U.S. PATENT DOCUMENTS

| | | | |
|---|---|---|---|
| 5,900,488 A | 5/1999 | Kodama et al. | |
| 6,585,963 B1 | 7/2003 | Quan et al. | |
| 8,193,232 B2 * | 6/2012 | Vontz ................. | A61K 31/4178 514/397 |
| 8,193,233 B2 * | 6/2012 | Vontz ................. | A61K 47/14 514/397 |
| 8,362,059 B2 * | 1/2013 | Vontz ................. | A61K 31/4178 514/397 |
| 8,980,931 B1 * | 3/2015 | Masuda ............. | A61K 31/4178 514/397 |
| 10,130,610 B2 | 11/2018 | Kobayashi et al. | |
| 2009/0030059 A1 | 1/2009 | Miki et al. | |
| 2009/0076109 A1 | 3/2009 | Miki et al. | |
| 2009/0137651 A1 | 5/2009 | Kobayashi et al. | |
| 2010/0168200 A1 * | 7/2010 | Masuda ............. | A61K 9/0014 514/397 |
| 2010/0173965 A1 | 7/2010 | Masuda et al. | |
| 2010/0204293 A1 | 8/2010 | Masuda et al. | |
| 2010/0210702 A1 | 8/2010 | Vontz et al. | |
| 2010/0210703 A1 | 8/2010 | Vontz et al. | |
| 2012/0014893 A1 | 1/2012 | Kobayashi et al. | |
| 2012/0015997 A1 | 1/2012 | Miki et al. | |
| 2012/0022120 A1 | 1/2012 | Kobayashi et al. | |
| 2012/0071533 A1 | 3/2012 | Vontz et al. | |
| 2012/0149745 A1 | 6/2012 | Kobayashi et al. | |
| 2012/0329845 A1 | 12/2012 | Masuda et al. | |
| 2013/0011351 A2 | 1/2013 | Kobayashi et al. | |
| 2013/0090365 A1 | 4/2013 | Kubota et al. | |
| 2013/0096187 A1 | 4/2013 | Kobayashi et al. | |
| 2013/0123318 A1 | 5/2013 | Vontz et al. | |
| 2015/0073028 A1 | 3/2015 | Masuda et al. | |
| 2015/0238606 A1 * | 8/2015 | Masuda ............. | A61K 47/10 514/397 |
| 2016/0361299 A1 | 12/2016 | Masuda et al. | |
| 2017/0071911 A1 | 3/2017 | Kobayashi et al. | |

FOREIGN PATENT DOCUMENTS

| | | |
|---|---|---|
| JP | H06-211651 A | 8/1994 |
| JP | H10-152433 A | 6/1998 |
| JP | 3278738 B2 | 4/2002 |
| JP | 2004-529923 A | 9/2004 |
| JP | 3803393 B2 | 8/2006 |
| JP | 2012-518009 A | 8/2012 |
| JP | 2012-523409 A | 10/2012 |
| JP | 5160409 B2 | 3/2013 |
| JP | 5184341 B2 | 4/2013 |
| JP | 5184342 B2 | 4/2013 |
| JP | 5345937 B2 | 11/2013 |
| JP | 5453093 B2 | 3/2014 |
| JP | 5529539 B2 | 6/2014 |
| JP | 5635075 B2 | 12/2014 |

(Continued)

OTHER PUBLICATIONS

Zaias, Nardo. "Onychomycosis." The nail in health and disease. Springer, Dordrecht, 1980. 91-113.*
International Search Report issued in PCT/JP2020/030350; dated Sep. 15, 2020.
Written Opinion issued in PCT/JP2020/030350; dated Sep. 15, 2020.

*Primary Examiner* — Bethany P Barham
*Assistant Examiner* — Peter Anthopolos
(74) *Attorney, Agent, or Firm* — Studebaker & Brackett PC

(57) ABSTRACT

The present invention provides a technique that allows a pharmaceutical composition, preferably for external use, containing luliconazole or the like to contain luliconazole or the like at a high concentration, and suppresses the precipitation thereof over time. The present invention uses a polyethylene glycol having an average molecular weight of 380 to 420 represented by a formula $HOCH_2(CH_2OCH_2)_nCH_2OH$ (where n is an integer), ethanol, benzyl alcohol, lactic acid, propylene carbonate, and acetone in combination with the luliconazole or the like.

25 Claims, No Drawings

(56) References Cited

FOREIGN PATENT DOCUMENTS

| | | |
|---|---:|---|
| JP | 5654497 B2 | 1/2015 |
| JP | 5688405 B2 | 3/2015 |
| JP | 5688406 B2 | 3/2015 |
| JP | 2015-114210 A | 6/2015 |
| JP | 5832451 B2 | 12/2015 |
| JP | 5938497 B2 | 6/2016 |
| WO | 96/11710 A1 | 4/1996 |

* cited by examiner

PHARMACEUTICAL COMPOSITION CONTAINING ANTIFUNGAL AGENT AS ACTIVE INGREDIENT

TECHNICAL FIELD

The present invention relates to a pharmaceutical composition containing an antifungal agent as an active ingredient for the purpose of treating or preventing onychomycosis.

BACKGROUND ART

Onychomycosis is a stubborn nail disease which is caused by dermatophytes, and involves symptoms such as turbidity, thickening, destruction, and deformation of the nail plate. Onychomycosis infects humans in public baths and other places, and does not heal naturally. It is estimated that about half of the patients with onychomycosis are untreated. In addition, even under treatment, it is difficult to deliver a pharmaceutical composition to the nail bed because the nail plate is dense and stiff, and in particular the toenail is much thicker than the fingernail. Therefore, the complete cure may take half a year or more, or one year or more.

Currently, oral drugs to treat onychomycosis have also been developed. However, since side effects occur and symptoms often recur even once being cured, external pharmaceutical compositions containing antifungal agents as active ingredients are mainly used.

An external pharmaceutical composition obtained by dissolving an antifungal agent for the purpose of treating or preventing onychomycosis, such as luliconazole or a pharmaceutically acceptable salt thereof (hereinafter also referred to as luliconazole or the like), is known (Patent Literature 1), and formulations with a concentration of 1% and formulations with a concentration of 0.5 to 5% have been put into practical use.

As ingredients of external pharmaceutical compositions obtained by dissolving antifungal agents for the purpose of treating or preventing onychomycosis, film forming agents, absorption enhancers, solubilizers, solvents, and the like have been researched, and there are many patents (Patent Literatures 2 to 13).

The film forming agents include alkyd resins, butyl acrylate-methacrylic acid copolymers, and the like (Patent Literature 14), or a mixture of copolymer AMP and ethanol, such as a mixture of acrylic (alkyl acrylate/diacetone acrylamide) copolymer AMP and ethanol.

The absorption enhancers include urea, salicylic acid, diisopropyl myristate, N-methyl-2-pyrrolidone, diisopropyl adipate (Patent Literature 15), dimethylformamide, dimethyl sulfoxide (Patent Literature 3), propylene glycol, and the like.

The solubilizers include acetone, propylene carbonate, benzyl alcohol, triacetin, lactic acid, crotamiton (Patent Literature 15), and the like.

The solvents include ethyl acetate, butyl acetate, ethanol, isopropanol, diisopropyl sebacate (Patent Literatures 14 and 16), diethylene glycol dibutyl ether (Patent Literature 17), xylene, dimethylacetamide, and the like.

CITATION LIST

Patent Literature

[Patent Literature 1] Japanese Patent No. 3278738
[Patent Literature 2] Japanese Patent No. 5160409
[Patent Literature 3] Japanese Patent No. 5184341
[Patent Literature 4] Japanese Patent No. 5184342
[Patent Literature 5] Japanese Patent No. 5688405
[Patent Literature 6] Japanese Patent No. 5635075
[Patent Literature 7] Japanese Patent No. 5529539
[Patent Literature 8] Japanese Patent No. 5345937
[Patent Literature 9] Japanese Patent No. 5453093
[Patent Literature 10] Japanese Patent No. 5688406
[Patent Literature 11] Japanese Patent No. 5832451
[Patent Literature 12] Japanese Patent No. 5938497
[Patent Literature 13] Japanese Patent No. 5654497
[Patent Literature 14] Japanese Patent No. 3803393
[Patent Literature 15] International Publication No. 1996/11710
[Patent Literature 16] Japanese Patent Application Publication No. Hei 6-211651
[Patent Literature 17] Published Japanese Translation of PCT International Application No. 2004-529923

SUMMARY OF INVENTION

Technical Problems

As described above, practically used external pharmaceutical compositions obtained by dissolving luliconazole or the like for the purpose of treating or preventing onychomycosis have a concentration of up to 5%. In order to seek further improvement of the therapeutic effects, higher concentration and stabilization are desired. However, it is known that compositions containing more than 5% of luliconazole or the like are unstable, and luliconazole or the like precipitate from the solution during storage and after application to the nail.

The present invention provides a technique that allows a pharmaceutical composition, preferably for external use, containing luliconazole or the like to contain luliconazole or the like at a high concentration, and suppresses the precipitation thereof over time.

Solution to Problems

In view of the above circumstances, the present inventors examined combinations of solvents that dissolve luliconazole or the like at a high concentration stably over time, and have found as a result that a polyethylene glycol having an average molecular weight of 380 to 420 represented by a formula $HOCH_2(CH_2OCH_2)_nCH_2OH$ (where n is an integer) can stably dissolve luliconazole or the like at a high concentration, and that the use of ethanol, benzyl alcohol, lactic acid, propylene carbonate, and acetone in combination with luliconazole or the like makes it possible to improve the solubility of luliconazole or the like and to suppress the precipitation thereof over time. These findings have led to the completion of the present invention.

Specifically, the present invention is as follows.

[1] A pharmaceutical composition containing luliconazole or a pharmaceutically acceptable salt thereof as an active ingredient, the pharmaceutical composition comprising:
  5 to 12% by mass of the luliconazole or the pharmaceutically acceptable salt thereof relative to a total mass of the pharmaceutical composition;
  a polyethylene glycol having an average molecular weight of 380 to 420 represented by a formula $HOCH_2(CH_2OCH_2)_nCH_2OH$ where n is an integer;
  ethanol;
  benzyl alcohol;
  lactic acid;
  propylene carbonate; and
  acetone.

[2] The pharmaceutical composition according to [1] described above, wherein the luliconazole or the pharmaceutically acceptable salt thereof is contained at 7 to 10% by mass relative to the total mass of the pharmaceutical composition.

[3] The pharmaceutical composition according to [1] or [2] described above, wherein the polyethylene glycol having an average molecular weight of 380 to 420 represented by the formula $HOCH_2(CH_2OCH_2)_nCH_2OH$ where n is an integer is contained at 5 to 40% by mass relative to the total mass of the pharmaceutical composition.

[4] The pharmaceutical composition according to any one of [1] to [3] described above, wherein the ethanol is contained at 20 to 70% by mass relative to the total mass of the pharmaceutical composition.

[5] The pharmaceutical composition according to [4] described above, wherein the ethanol is contained at 30% by mass or more and less than 50% by mass relative to the total mass of the pharmaceutical composition.

[6] The pharmaceutical composition according to any one of [1] to [5] described above, wherein the benzyl alcohol is contained at 0.01 to 10% by mass relative to the total mass of the pharmaceutical composition.

[7] The pharmaceutical composition according to any one of [1] to [6] described above, wherein the lactic acid is contained at 1 to 10% by mass relative to the total mass of the pharmaceutical composition.

[8] The pharmaceutical composition according to any one of [1] to [7] described above, wherein the propylene carbonate is contained at 1 to 15% by mass relative to the total mass of the pharmaceutical composition.

[9] The pharmaceutical composition according to any one of [1] to [8] described above, wherein the acetone is contained at 1 to 25% by mass relative to the total mass of the pharmaceutical composition.

[10] The pharmaceutical composition according to any one of [1] to [9] described above, further comprising isopropyl myristate.

[11] The pharmaceutical composition according to [10] described above, wherein the isopropyl myristate is contained at 1 to 10% by mass relative to the total mass of the pharmaceutical composition.

[12] The pharmaceutical composition according to any one of [1] to [11] described above, further comprising a film forming agent.

[13] The pharmaceutical composition according to [12] described above, wherein the film forming agent contains a mixture of an acrylic resin alkanolamine and ethanol, or a mixture of (alkyl acrylate/diacetone acrylamide) copolymer AMP and ethanol.

[14] The pharmaceutical composition according to [12] or [13] described above, wherein the film forming agent is contained at 0.01 to 4% by mass relative to the total mass of the pharmaceutical composition.

[15] The pharmaceutical composition according to any one of [1] to [14] described above, further comprising N-methyl-2-pyrrolidone.

[16] The pharmaceutical composition according to any one of [1] to [14] described above, which is free of N-methyl-2-pyrrolidone.

[17] The pharmaceutical composition according to any one of [1] to [16] described above, for treating or preventing onychomycosis.

[18] The pharmaceutical composition according to [17] described above, wherein the onychomycosis is distal subungual onychomycosis.

[19] The pharmaceutical composition according to [17] or [18] described above, wherein the onychomycosis is an infection of toenails.

[20] The pharmaceutical composition according to [17] or [18] described above, wherein the onychomycosis is an infection of fingernails.

[21] The pharmaceutical composition according to any one of [1] to [20] described above, which is an external medicine.

[22] The pharmaceutical composition according to [21] described above, which is applied to an affected area once a day.

[23] A method of preparing the pharmaceutical composition according to any one of [1] to [22] described above, the method comprising mixing the luliconazole or the pharmaceutically acceptable salt thereof with the polyethylene glycol having an average molecular weight of 380 to 420 represented by the formula $HOCH_2(CH_2OCH_2)_nCH_2OH$ where n is an integer, the ethanol, the benzyl alcohol, the lactic acid, the propylene carbonate, and the acetone.

Effects of Invention

The present invention makes it possible to provide a pharmaceutical composition, preferably for external use, which has luliconazole or the like dissolved therein at a high concentration and can be stored for a long period of time thanks to stability over time and no precipitation of luliconazole or the like. The pharmaceutical composition of the present invention may preferably contain 5% by mass or more, and more preferably 10% by mass of luliconazole or the like.

DESCRIPTION OF EMBODIMENTS

The present invention relates to a pharmaceutical composition containing luliconazole or a pharmaceutically acceptable salt thereof as an active ingredient, the pharmaceutical composition comprising: 5 to 12% by mass of the luliconazole or the pharmaceutically acceptable salt thereof relative to a total mass of the pharmaceutical composition; a polyethylene glycol having an average molecular weight of 380 to 420 represented by a formula $HOCH_2(CH_2OCH_2)_nCH_2OH$ (where n is an integer); ethanol; benzyl alcohol; lactic acid; propylene carbonate; and acetone.

The pharmaceutical composition of the present invention contains luliconazole or the like as an active ingredient.

Luliconazole is a known compound represented by the chemical name (R)-(−)-(E)-[4-(2,4-dichlorophenyl)-1,3-dithiolane-2-ylidene]-1-imidazolylacetonitrile, and its production method and antifungal properties are already known. In addition, the "pharmaceutically acceptable salt" is not particularly limited as long as it is physiologically acceptable, and preferable examples thereof can include mineral acid salts such as hydrochlorides, nitrates, sulfates, and phosphates, organic acid salts such as citrates, oxalates, lactates, and acetates, and sulfate-containing salts such as mesylates and tosylates. From the viewpoint of safety and solubility, hydrochlorides are more preferable.

In the pharmaceutical composition of the present invention, the content of luliconazole or the like is 5 to 12% by mass, may be preferably more than 5% by mass, more preferably 6 to 11% by mass, 7 to 10% by mass, 8 to 10% by mass, or 9 to 10% by mass, and particularly preferably 10% by mass relative to the total mass of the pharmaceutical composition. The higher the content of luliconazole or the like, the higher the therapeutic effects can be expected. When the content of luliconazole or the like is 12% by mass or less, the precipitation thereof can be suppressed over time according to the present invention. The content of luliconazole or the like can be appropriately determined within the above ranges depending on the solubility in the solvent used.

The compound represented by the formula $HOCH_2(CH_2OCH_2)_nCH_2OH$ (where n is an integer) is known as a polyethylene glycol (or also called macrogol or PEG), and is a readily available compound. The compound can be prepared by, for example, addition polymerization of ethylene oxide and water. Compounds having an average molecular weight of 190 to 25000 are widely used also as pharmaceutical additives. Among them, polyethylene glycol 200 having an average molecular weight of 190 to 210, polyethylene glycol 300 having an average molecular weight of 285 to 315, polyethylene glycol 400 having an average molecular weight of 380 to 420, and polyethylene glycol 600 having an average molecular weight of 570 to 630 exists as a liquid at standard temperature, and are suitable for producing a liquid agent. Compounds having an average molecular weight greater than 630 are not preferable because they exist as a solid at standard temperature and may thus pose concerns of turbidity or precipitation when mixed with a liquid agent. The pharmaceutical composition of the present invention contains a polyethylene glycol having an average molecular weight of 380 to 420, which best dissolves luliconazole or the like. The content of the polyethylene glycol having an average molecular weight of 380 to 420 is preferably 5 to 40% by mass, more preferably 6 to 30% by mass, and further preferably 8 to 20% by mass relative to the total mass of the pharmaceutical composition. The average molecular weight in the invention of the present application means a number average molecular weight, and can be calculated based on a hydroxyl value measured in accordance with JIS K1557-1.

The pharmaceutical composition of the present invention contains ethanol as a solvent. The pharmaceutical composition may optionally contain, in addition to ethanol, a conventionally known solvent such as ethyl acetate, butyl acetate, isopropanol, diisopropyl sebacate, diethylene glycol dibutyl ether, xylene, and dimethylacetamide. The amount of ethanol blended is, for example, 20 to 70% by mass, preferably 30 to 68% by mass, and more preferably 40 to 65% by mass relative to the total mass of the pharmaceutical composition. Alternatively, the amount of ethanol blended may be less than 50% by mass, for example, 30% by mass or more and less than 50% by mass relative to the total mass of the pharmaceutical composition. When the ingredients other than the solvent (for example, the film forming agent) contain ethanol, the amount of ethanol blended means the total amount of ethanol contained in the solvent and the ingredients other than the solvent.

The solubilizer forms a complex with luliconazole or the like to increase the solubility, and there are many types such as benzyl alcohol, acetone, glycerin, lactic acid, crotamiton, propylene carbonate, urea, and propylene glycol. The pharmaceutical composition of the present invention contains benzyl alcohol, lactic acid, propylene carbonate, and acetone. The above-described specific combination of solubilizers contained increases the solubility of luliconazole or the like and the stability of the pharmaceutical composition, and also improves the absorbability of the active ingredients (permeability to the nail). In the pharmaceutical composition of the present invention, the amount of the solubilizers blended is desirably determined by the solubility of luliconazole and its formulation properties (for example, volatility and permeability to the nail). For example, relative to the total mass of the pharmaceutical composition, benzyl alcohol may be contained at 0.01 to 10% by mass, 0.5 to 8% by mass, or 1 to 6% by mass, lactic acid may be contained at 1 to 10% by mass, 2 to 8% by mass, or 3 to 6% by mass, propylene carbonate may be contained at 1 to 15% by mass, 2 to 10% by mass, or 3 to 7.5% by mass, and acetone may be contained at 1 to 25% by mass, 2 to 15% by mass, or 3 to 10% by mass. In addition to benzyl alcohol, lactic acid, propylene carbonate, and acetone, the pharmaceutical composition of the present invention can be blended with a known solubilizer (such as glycerin, crotamiton, urea, and propylene glycol).

For example, the pharmaceutical composition of the present invention contains 5 to 12% by mass of luliconazole or a pharmaceutically acceptable salt thereof, 5 to 40% by mass of a polyethylene glycol having an average molecular weight of 380 to 420 represented by the formula $HOCH_2(CH_2OCH_2)_nCH_2OH$ (where n is an integer), 20 to 70% by mass of ethanol, 0.01 to 10% by mass of benzyl alcohol, 1 to 10% by mass of lactic acid, 1 to 15% by mass of propylene carbonate, and 1 to 25% by mass of acetone relative to the total mass of the pharmaceutical composition.

The pharmaceutical composition of the present invention may contain a film forming agent as an optional ingredient. The film forming agent has a film forming ability after the pharmaceutical composition is applied to the affected area and dried, and contains a solvent and an additive. The additive includes, for example, copolyvidone, povidone, hydroxypropyl cellulose, hypromellose, polyvinyl alcohol polymer, acrylic resin alkanolamine, polyvinyl acetal diethylaminoacetate, (alkyl acrylate/diacetone acrylamide) copolymer AMP, and the like. The solvent includes lower alcohols such as methanol, ethanol, and isopropanol, ethyl acetate, butyl acetate, and the like. As the film forming agent, it is possible preferably to use a mixture of an acrylic resin alkanolamine and ethanol (acrylic resin alkanolamine solution), or a mixture of (alkyl acrylate/diacetone acrylamide) copolymer AMP (salt of 2-amino-2-methyl-1propanol with a copolymer of alkyl acrylate and diacetone acrylamide) and ethanol. In the pharmaceutical composition of the present invention, the total amount of the film forming agent blended is, for example, 0.01 to 10% by mass, preferably 0.01 to 6% by mass, and more preferably 0.01 to 4% by mass relative to the total amount of the pharmaceutical composition. The above ranges are preferable because, when the amount of the film forming agent blended is 0.01% by mass or more, sufficient film formation is achieved, and when the amount of the film forming agent blended is 10% by mass or less, the concentration of the antifungal agent in the film is relatively high.

The pharmaceutical composition of the present invention may contain, for example, an absorption enhancer such as isopropyl myristate or N-methyl-2-pyrrolidone as an optional ingredient, but is preferably free of N-methyl-2-pyrrolidone from the viewpoint of safety. The absorption enhancer can improve the absorbability of active ingredients by coexisting with the active ingredients. In the pharmaceutical composition of the present invention, the amount of the absorption enhancer blended is desirably determined in consideration of sufficient absorption enhancing effects and skin irritation. For example, the amount of the absorption enhancer blended may be 1 to 10% by mass relative to the mass of the pharmaceutical composition.

In addition to the above ingredients, the pharmaceutical composition of the present invention may be blended with an optional ingredient that is usually used in a pharmaceutical composition as long as the effects of the present invention are not impaired. Examples of such an optional ingredient include ingredients that can be generally used for external medicines such as diisopropyl adipate, 1,3-butylene glycol, and medium-chain fatty acid triglycerides.

The pharmaceutical composition of the present invention is preferably an external medicine. The dosage form of the pharmaceutical composition is not particularly limited as long as it is conventionally used as an external pharmaceutical composition. For example, formulation as a lotion, cream, gel, or the like is possible.

The pharmaceutical composition of the present invention can be prepared by a known method of preparing an external medicine, for example by mixing ingredients to be blended. There is no limitation on e.g. the means and order of mixing, and it is possible to prepare the pharmaceutical composition of the present invention by, for example, mixing luliconazole or the like with the polyethylene glycol having an average molecular weight of 380 to 420 represented by the formula $HOCH_2(CH_2OCH_2)_nCH_2OH$ (where n is an integer), ethanol, benzyl alcohol, lactic acid, propylene carbonate, and acetone as well as an optional additional ingredient.

The pharmaceutical composition of the present invention can be used for treating or preventing onychomycosis such as candidal onychomycosis and tinea. Onychomycosis includes distal subungual onychomycosis such as distal and lateral subungual onychomycosis, superficial white onychomycosis, and proximal subungual onychomycosis, and the pharmaceutical composition of the present invention is particularly useful for treating or preventing distal and lateral subungual onychomycosis. Examples of fungi that cause onychomycosis include *Trichophyton rubrum* and *Trichophyton mentagrophytes*. Onychomycosis may be a toenail infection or a fingernail infection.

The dosage and administration of the pharmaceutical composition of the present invention can be appropriately adjusted according to the symptoms, but it is preferable to apply the composition in an appropriate amount, for example, 10 to 12 mg/cm² to the affected area once a day. In addition, it is preferable to apply the composition every day until the nail of the affected area completely regrows.

Examples

Hereinafter, the present invention is described in more detail with reference to Examples, but the present invention is not limited to these examples.

<Test on Solubility to Polyethylene Glycol>

Examined was how luliconazole is dissolved by polyethylene glycol 200 having an average molecular weight of 190 to 210, polyethylene glycol 300 having an average molecular weight of 285 to 315, polyethylene glycol 400 having an average molecular weight of 380 to 420, and polyethylene glycol 600 having an average molecular weight of 570 to 630, each of which is represented by the formula $HOCH_2(CH_2OCH_2)_nCH_2OH$ (where n is an integer). To this end, the above polyethylene glycols (manufactured by NOF Corporation) were mixed with luliconazole according to the formulation presented in Table 1 below, and the properties of the solution (presence of insoluble matter (luliconazole)) were visually evaluated. Table 1 presents the results (values in the table are in g).

TABLE 1

| Ingredient | Prescription | | | | | | | | |
|---|---|---|---|---|---|---|---|---|---|
| | 1 | 2 | 3 | 4 | 5 | 6 | 7 | 8 | 9 |
| Polyethylene Glycol 200 | 10 | 10 | | | | | | | |
| Polyethylene Glycol 300 | | | 10 | 10 | 10 | | | | |
| Polyethylene Glycol 400 | | | | | | 10 | 10 | | |
| Polyethylene Glycol 600 | | | | | | | | 10 | 10 |
| Luliconazole | 0.5 | 0.7 | 0.5 | 0.7 | 0.9 | 0.5 | 1 | 0.1 | 0.2 |
| Properties of Solution | o | x | o | o | x | o | o | o | x |

Notation for Properties of Solution;
o: no insoluble matter observed,
x: insoluble matter observed.

As illustrated in Table 1, polyethylene glycols 200, 300, 400, and 600 have a high solubility for luliconazole. Moreover, it is understood that polyethylene glycol 400 has the highest solubility for luliconazole compared to polyethylene glycol 200, polyethylene glycol 300, and polyethylene glycol 600.

<Solubility and Storage Stability of Luliconazole>

For polyethylene glycol 400 having an average molecular weight of 380 to 420 represented by the formula $HOCH_2(CH_2OCH_2)_nCH_2OH$ (where n is an integer), pharmaceutical compositions containing one to three of benzyl alcohol, lactic acid, propylene carbonate, and acetone (formulations 1 to 14) and a pharmaceutical compositions of the present invention containing all four (formulations 15 to 22) were produced in accordance with the prescriptions in Table 2 below. Specifically, ingredients other than luliconazole were stirred at room temperature, and luliconazole was added and dissolved to obtain a lotion agent. Note that the numerical values in the table are indicated in % by mass. The properties of the solution (presence or absence of insoluble matter (luliconazole)) and the presence or absence of precipitation of luliconazole crystals after air drying were evaluated immediately after production and after storage for a predetermined period at 25° C., 5° C. and 60° C. The properties of the solution were checked with the naked eye, and for the crystal precipitation after air drying, a lotion was dropped on a glass slide, naturally dried, and observed with a microscope. In the formulations 1 to 14, insoluble matters were observed immediately after production, or crystal precipitation was confirmed after air drying, so that the storage stability was not confirmed. Table 3 presents the results.

TABLE 2

| Ingredient | Formulation | | | | | | | | | | | | | | | | | | | | | |
|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| Luliconazole | 10 | 10 | 10 | 10 | 10 | 10 | 10 | 10 | 10 | 10 | 10 | 10 | 10 | 10 | 10 | 10 | 10 | 10 | 10 | 10 | 10 | 10 |
| Polyethylene Glycol 400 | 10 | 10 | 10 | 10 | 10 | 10 | 10 | 10 | 10 | 10 | 10 | 10 | 10 | 10 | 10 | 10 | 10 | 10 | 10 | 20 | 10 | 10 |
| Benzyl Alcohol | 20 | | | | 10 | 10 | 10 | | | | 6.67 | 6.67 | 6.67 | | 5 | 4 | 4 | 4 | 6 | 6 | 6 | 6 |
| Lactic Acid | 20 | | | 10 | | | 10 | 10 | | | 6.67 | 6.67 | | 6.67 | 5 | 4 | 5 | 6 | 4 | 6 | 6 | 6 |
| Propylene Carbonate | 20 | | 10 | | | 10 | | 10 | | 6.67 | | 6.67 | 6.67 | 5 | 5 | 6 | 5 | 5 | 6 | 6 | 6 | |
| Acetone | 20 | | | | 10 | | 10 | 10 | | | 6.67 | 6.67 | 6.67 | 5 | 6 | 4 | 4 | 6 | 6 | 6 | 6 | |
| Isopropyl Myristate | | | | | | | | | | | | | | | | | | | | | 8 | |
| Acrylic Resin Alkanolamine Solution | | | | | | | | | | | | | | | | | | | | | | 1 |
| Absolute Ethanol | 60 | 60 | 60 | 60 | 60 | 60 | 60 | 60 | 60 | 60 | 60 | 60 | 60 | 60 | 60 | 61 | 61 | 61 | 61 | 46 | 48 | 55 |

TABLE 3

| | | Formulation | | | | | | | | | | | | | | | | | | | | | |
|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| Properties of Solution Immediately After Production | | x | x | o | o | x | o | o | o | o | o | o | o | o | o | o | o | o | o | o | o | o | o |
| Presence or Absence of Precipitation of Crystals After Air Drying | | x | x | x | x | x | x | x | x | x | x | x | x | x | x | o | o | o | o | o | o | o | o |
| Presence or Absence of Insoluble Matter under Storage | | | | | | | | | | | | | | | | | | | | | | | |
| 25° C. | 1 Week | — | — | — | — | — | — | — | — | — | — | — | — | — | — | o | o | o | o | o | o | o | o |
| | 2 Weeks | — | — | — | — | — | — | — | — | — | — | — | — | — | — | o | o | o | o | o | o | o | o |
| | 3 Weeks | — | — | — | — | — | — | — | — | — | — | — | — | — | — | o | o | o | o | o | o | o | o |
| 5° C. | 5 Days | — | — | — | — | — | — | — | — | — | — | — | — | — | — | o | o | o | o | o | o | o | o |
| | 1 Week | — | — | — | — | — | — | — | — | — | — | — | — | — | — | o | o | o | o | o | o | o | o |
| | 2 Weeks | — | — | — | — | — | — | — | — | — | — | — | — | — | — | o | o | o | o | o | o | o | o |
| | 3 Weeks | — | — | — | — | — | — | — | — | — | — | — | — | — | — | o | o | o | o | o | o | o | o |
| 60° C. | 3 Weeks | — | — | — | — | — | — | — | — | — | — | — | — | — | — | o | o | o | o | o | o | o | o |
| Presence or Absence of Precipitation of Crystals After Air Drying | | | | | | | | | | | | | | | | | | | | | | | | |
| 25° C. | 1 Week | — | — | — | — | — | — | — | — | — | — | — | — | — | — | o | o | o | o | o | o | o | o |
| | 2 Weeks | — | — | — | — | — | — | — | — | — | — | — | — | — | — | o | o | o | o | o | o | o | o |
| | 3 Weeks | — | — | — | — | — | — | — | — | — | — | — | — | — | — | o | o | o | o | o | o | o | o |
| 5° C. | 5 Days | — | — | — | — | — | — | — | — | — | — | — | — | — | — | o | o | o | o | o | o | o | o |
| | 1 Week | — | — | — | — | — | — | — | — | — | — | — | — | — | — | o | o | o | o | o | o | o | o |
| | 2 Weeks | — | — | — | — | — | — | — | — | — | — | — | — | — | — | o | o | o | o | o | o | o | o |
| | 3 Weeks | — | — | — | — | — | — | — | — | — | — | — | — | — | — | o | o | o | o | o | o | o | o |
| 60° C. | 3 Weeks | — | — | — | — | — | — | — | — | — | — | — | — | — | — | o | o | o | o | o | o | o | o |

Notation for Properties of Solution;
o: no insoluble matter observed,
x: insoluble matter observed,
—: no test carried out.
Notation for Presence or Absence of Precipitation of Crystals After Air Drying;
o: no crystal precipitation observed,
x: crystal precipitation observed,
—: no test carried out.

In a similar manner, Table 4 was obeyed to also prepare comparative formulations 1 to 6 containing no polyethylene glycol as well as comparative formulations 7 to 27 using polyethylene glycol 200 having an average molecular weight of 190 to 210, polyethylene glycol 300 having an average molecular weight of 285 to 315, polyethylene glycol 600 having an average molecular weight of 570 to 630, polyethylene glycol 1000 having an average molecular weight of 950 to 1050 each of which is represented by the formula $HOCH_2(CH_2OCH_2)_nCH_2OH$ (where n is an integer), polyethylene glycol 1500 which is a mixture of equal amounts of polyethylene glycol 300 and polyethylene glycol 1540, polyethylene glycol 1540 having an average molecular weight of 1300 to 1600, polyethylene glycol 4000 having an average molecular weight of 2600 to 3800, polyethylene glycol 6000 having an average molecular weight of 7300 to 9300, and polyethylene glycol 20000 having an average molecular weight of 15000 to 25000. The properties of the solution (presence or absence of insoluble matter (luliconazole)) and the presence or absence of precipitation of luliconazole crystals after air drying were checked with the naked eye and under the microscope in the same manner as the formulations 1 to 22 immediately after production and after storage for a predetermined period of time at 25° C., 5° C., and 60° C. Note that, in the comparative formulations 1 to 4, insoluble matters were observed immediately after production, so that the storage stability was not confirmed. Table 5 presents the results.

TABLE 4

| Ingredient | Comparative Formulation | | | | | | | | | | | | | | | | | | | | | | | | | | |
|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
| Luliconazole | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 |
| Benzyl Alcohol | | 2 | 4 | 4 | 2 | 2 | 4 | 4 | 4 | 4 | 4 | 4 | 4 | 4 | 4 | 4 | 4 | 4 | 4 | 4 | 4 | 4 | 4 | 4 | 4 | 4 | 4 |
| Polyethylene Glycol 200 | | | | | | | | | | | | | | | | | | | 10 | | | 10 | | | 10 | | |
| Polyethylene Glycol 300 | | | | | | | | | | | | | | | | | | | | 10 | | | 10 | | | 10 | |
| Polyethylene Glycol 600 | | | | | | | | | | | | | | | | | | | | | 10 | | | 10 | | | 10 |
| Polyethylene Glycol 1000 | | | | | | | 1 | 10 | | | | | | | | | | | | | | | | | | | |
| Polyethylene Glycol 1500 | | | | | | | | | 1 | 10 | | | | | | | | | | | | | | | | | |
| Polyethylene Glycol 1540 | | | | | | | | | | | 1 | 10 | | | | | | | | | | | | | | | |
| Polyethylene Glycol 4000 | | | | | | | | | | | | | 1 | 10 | | | | | | | | | | | | | |
| Polyethylene Glycol 6000 | | | | | | | | | | | | | | | 1 | 10 | | | | | | | | | | | |
| Polyethylene Glycol 20000 | | | | | | | | | | | | | | | | | 1 | 10 | | | | | | | | | |
| Lactic Acid | 8 | 4 | 4 | 4 | 6 | 4 | 4 | 4 | 4 | 4 | 4 | 4 | 4 | 4 | 4 | 4 | 4 | 4 | 4 | 4 | 4 | 4 | 4 | 4 | 4 | 4 | 4 |
| Propylene Carbonate | | | | | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
| Propylene Glycol | | | | | 10 | | | | | | | | | | | | | | | | | | | | | | |
| Acetone | | 6 | 6 | 6 | 10 | 10 | 6 | 6 | 6 | 6 | 6 | 6 | 6 | 6 | 6 | 6 | 6 | 6 | 6 | 6 | 6 | 6 | 6 | 6 | 6 | 6 | 6 |
| Diisopropyl Adipate | | | 12 | 12 | | | | | | | | | | | | | | | | | | | | | | | |
| Isopropyl Myristate | | | | | 8 | 8 | 8 | 8 | 8 | 8 | 8 | 8 | 8 | 8 | 8 | 8 | 8 | 8 | 8 | 8 | 8 | | | | | | |
| N-Methyl-2-Pyrrolidone | | | | 8 | 4 | 4 | 4 | 4 | 4 | 4 | 4 | 4 | 4 | 4 | 4 | 4 | 4 | 4 | 4 | 4 | 4 | | | | | | |
| Povidone | | | | 0.5 | | | | | | | | | | | | | | | | | | | | | | | |
| Acrylic Resin Alkanolamine Solution | | | | | | | 1 | 1 | 1 | 1 | 1 | 1 | 1 | 1 | 1 | 1 | 1 | 1 | 1 | 1 | 1 | | | | | | |
| Absolute Ethanol | 82 | 78 | 64 | 55.5 | 57 | 69 | 57 | 48 | 57 | 48 | 57 | 48 | 57 | 48 | 57 | 48 | 57 | 48 | 61 | 61 | 61 | 49 | 49 | 49 | 48 | 48 | 48 |

| | | Comparative Formulation | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
| Properties of Solution Immediately After Production | | x | x | x | x | ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ |
| Presence or Absence of Precipitation of Crystals After Air Drying | | x | x | x | x | ○ | ○ | ○ | ○ | x | ○ | ○ | ○ | ○ | ○ | ○ | ○ | ○ | ○ | ○ | ○ | ○ | ○ | ○ | ○ | ○ | ○ | ○ |
| Presence or Absence of Insoluble Matter under Storage | | | | | | | | | | | | | | | | | | | | | | | | | | | | |
| 25° C. | 1 Week | — | — | — | — | ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ |
| | 2 Weeks | — | — | — | — | ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ |
| | 3 Weeks | — | — | — | — | ○ | ○ | x | ○ | ○ | ○ | ○ | ○ | ○ | ○ | ○ | ○ | ○ | ○ | ○ | ○ | ○ | ○ | ○ | ○ | ○ | ○ | ○ |
| 5° C. | 5 Days | — | — | — | — | ○ | ○ | ○ | ○ | ○ | x | ○ | x | x | x | x | x | x | x | ○ | ○ | ○ | ○ | ○ | ○ | ○ | ○ | ○ |
| | 1 Week | — | — | — | — | ○ | ○ | ○ | ○ | ○ | x | ○ | x | x | x | x | x | x | x | ○ | ○ | ○ | ○ | ○ | ○ | ○ | ○ | ○ |
| | 2 Weeks | — | — | — | — | x | x | ○ | ○ | ○ | x | ○ | x | x | x | x | x | x | x | ○ | ○ | ○ | ○ | ○ | ○ | ○ | ○ | ○ |
| | 3 Weeks | — | — | — | — | x | x | ○ | ○ | ○ | x | ○ | x | x | x | x | x | x | x | ○ | ○ | ○ | ○ | ○ | ○ | ○ | ○ | ○ |
| 60° C. | 3 Weeks | — | — | — | — | ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ |
| Presence or Absence of Precipitation of Crystals After Air Drying | | | | | | | | | | | | | | | | | | | | | | | | | | | | |
| 25° C. | 1 Week | — | — | — | — | ○ | ○ | ○ | ○ | ○ | ○ | ○ | ○ | ○ | ○ | ○ | ○ | ○ | ○ | ○ | ○ | ○ | ○ | ○ | ○ | ○ | ○ | ○ |
| | 2 Weeks | — | — | — | — | ○ | ○ | x | x | x | x | x | x | x | x | x | x | x | x | x | x | x | x | x | x | x | x | x |
| | 3 Weeks | — | — | — | — | ○ | x | x | x | x | x | x | x | x | x | x | x | x | x | x | x | x | x | x | x | x | x | x |

-continued

| | | Comparative Formulation | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
| 5° C. | 5 Days | — | — | — | — | — | o | o | x | x | x | x | x | x | x | x | x | x | x | x | o | o | o | o | o | o | o | o | o |
| | 1 Week | — | — | — | — | — | o | o | x | x | x | x | x | x | x | x | x | x | x | x | o | o | o | o | o | o | o | o | o |
| | 2 Weeks | — | — | — | — | x | x | x | x | x | x | x | x | x | x | x | x | x | x | x | x | x | x | x | x | x | x | x | x |
| | 3 Weeks | — | — | — | — | x | x | x | x | x | x | x | x | x | x | x | x | x | x | x | x | x | x | x | x | x | x | x | x |
| 60° C. | 3 Weeks | — | — | — | — | o | o | x | x | x | x | x | x | x | x | x | x | x | x | x | x | x | x | x | x | x | x | x | x |

Notation for Properties of Solution;
o: no insoluble matter observed,
x: insoluble matter observed,
—: no test carried out.
Notation for Presence or Absence of Precipitation of Crystals After Air Drying;
o: no crystal precipitation observed,
x: crystal precipitation observed,
—: no test carried out.

As presented in Table 3, in the formulations 15 to 22 in which all four types of benzyl alcohol, lactic acid, propylene carbonate, and acetone had been added to polyethylene glycol 400, insoluble matter and crystals after air drying did not precipitate immediately after production. In addition, also in the case of storage for a predetermined period under the conditions of 25° C., 5° C., and 60° C., the solubility was high and there was no insoluble matter or precipitation of crystals after air drying. Meanwhile, the comparative formulations 5 to 27 showed insoluble matter and/or precipitation of crystals after air drying under any of the storage conditions. In particular, in the comparative formulations 7 to 27 not using the polyethylene glycol having an average molecular weight of 380 to 420 as a polyethylene glycol represented by the formula $HOCH_2(CH_2OCH_2)_nCH_2OH$ (where n is an integer), precipitation of crystals was observed by air drying after storage even in the case of containing all four types of benzyl alcohol, lactic acid, propylene carbonate, and acetone as a solubilizer. This reveals that the pharmaceutical composition of the present invention can be stably stored over time.

INDUSTRIAL APPLICABILITY

The present invention makes it possible to provide an external pharmaceutical composition which dissolves luliconazole at a high concentration and can be stably stored over time.

The invention claimed is:

1. A pharmaceutical composition containing luliconazole or a pharmaceutically acceptable salt thereof as an active ingredient, the pharmaceutical composition comprising:
    7 to 12% by mass of the luliconazole or the pharmaceutically acceptable salt thereof relative to a total mass of the pharmaceutical composition;
    a polyethylene glycol having an average molecular weight of 380 to 420 represented by a formula $HOCH_2(CH_2OCH_2)_nCH_2OH$ where n is an integer;
    ethanol;
    benzyl alcohol;
    lactic acid;
    propylene carbonate; and
    3 to 10% by mass of acetone relative to a total mass of the pharmaceutical composition.

2. The pharmaceutical composition according to claim 1, wherein the luliconazole or the pharmaceutically acceptable salt thereof is contained at 7 to 10% by mass relative to the total mass of the pharmaceutical composition.

3. The pharmaceutical composition according to claim 1, wherein the polyethylene glycol having an average molecular weight of 380 to 420 represented by the formula $HOCH_2(CH_2OCH_2)_nCH_2OH$ where n is an integer is contained at 5 to 40% by mass relative to the total mass of the pharmaceutical composition.

4. The pharmaceutical composition according to claim 1, wherein the ethanol is contained at 20 to 70% by mass relative to the total mass of the pharmaceutical composition.

5. The pharmaceutical composition according to claim 4, wherein the ethanol is contained at 30% by mass or more and less than 50% by mass relative to the total mass of the pharmaceutical composition.

6. The pharmaceutical composition according to claim 1, wherein the benzyl alcohol is contained at 0.01 to 10% by mass relative to the total mass of the pharmaceutical composition.

7. The pharmaceutical composition according to claim 1, wherein the lactic acid is contained at 1 to 10% by mass relative to the total mass of the pharmaceutical composition.

8. The pharmaceutical composition according to claim 1, wherein the propylene carbonate is contained at 1 to 15% by mass relative to the total mass of the pharmaceutical composition.

9. The pharmaceutical composition according to claim 1, further comprising isopropyl myristate.

10. The pharmaceutical composition according to claim 9, wherein the isopropyl myristate is contained at 1 to 10% by mass relative to the total mass of the pharmaceutical composition.

11. The pharmaceutical composition according to claim 1, further comprising a film forming agent.

12. The pharmaceutical composition according to claim 11, wherein the film forming agent contains a mixture of an acrylic resin alkanolamine and ethanol, or a mixture of (alkyl acrylate/diacetone acrylamide) copolymer AMP and ethanol.

13. The pharmaceutical composition according to claim 11, wherein the film forming agent is contained at 0.01 to 4% by mass relative to the total mass of the pharmaceutical composition.

14. The pharmaceutical composition according to claim 1, further comprising N-methyl-2-pyrrolidone.

15. The pharmaceutical composition according to claim 1, which is free of N-methyl-2-pyrrolidone.

16. The pharmaceutical composition according to claim 1, which is an external medicine.

17. The pharmaceutical composition according to claim 1, wherein the benzyl alcohol is contained at 1 to 6% by mass relative to the total mass of the pharmaceutical composition.

18. The pharmaceutical composition according to claim 1, wherein the lactic acid is contained at 3 to 6% by mass relative to the total mass of the pharmaceutical composition.

19. The pharmaceutical composition according to claim 1, wherein the propylene carbonate is contained at 3 to 7.5% by mass relative to the total mass of the pharmaceutical composition.

20. A method for treating or preventing onychomycosis in a subject in need thereof, comprising applying a pharmaceutically effective amount of the pharmaceutical composition according to claim 1 to toenails or fingernails of the subject.

21. The method according to claim 20, wherein the onychomycosis is distal subungual onychomycosis.

22. The method according to claim 20, wherein the onychomycosis is an infection of toenails.

23. The method according to claim 20, wherein the onychomycosis is an infection of fingernails.

24. The method according to claim 20, wherein the pharmaceutical composition is applied to the toenails or fingernails once a day.

25. A method of preparing the pharmaceutical composition according to claim 1, the method comprising mixing the luliconazole or the pharmaceutically acceptable salt thereof with the polyethylene glycol having an average molecular weight of 380 to 420 represented by the formula $HOCH_2(CH_2OCH_2)_nCH_2OH$ where n is an integer, the ethanol, the benzyl alcohol, the lactic acid, the propylene carbonate, and the acetone.

\* \* \* \* \*